United States Patent
Dedecek et al.

(10) Patent No.: US 11,951,462 B2
(45) Date of Patent: Apr. 9, 2024

(54) USE OF A CATALYST FOR PRODUCTION OF METHANOL FROM METHANE, A METHOD OF PRODUCTION OF METHANOL FROM METHANE, THE CATALYST AND A METHOD OF PRODUCTION THEREOF

(71) Applicant: USTAV FYZIKALNI CHEMIE J. HEYROVSKEHO AV CR, V.V.I., Prague (CZ)

(72) Inventors: Jiri Dedecek, Prague (CZ); Edyta Tabor, Prague (CZ); Zdenek Sobalik, Prague (CZ); Stepan Sklenak, Prague (CZ); Kinga Mlekodaj, Rabka-Zdroj (PL)

(73) Assignee: USTAV FYZIKALNI CHEMIE J. HEYROVSKEHO AV CR, V.V.I., Prague (CZ)

( * ) Notice: Subject to any disclaimer, the term of this patent is extended or adjusted under 35 U.S.C. 154(b) by 395 days.

(21) Appl. No.: 17/600,878

(22) PCT Filed: Apr. 2, 2020

(86) PCT No.: PCT/CZ2020/050018
§ 371 (c)(1),
(2) Date: Oct. 1, 2021

(87) PCT Pub. No.: WO2020/200336
PCT Pub. Date: Oct. 8, 2020

(65) Prior Publication Data
US 2022/0168714 A1 Jun. 2, 2022

(30) Foreign Application Priority Data
Apr. 3, 2019 (CZ) .............. PV 2019-210

(51) Int. Cl.
*B01J 29/69* (2006.01)
*B01J 29/78* (2006.01)
*C07C 29/50* (2006.01)

(52) U.S. Cl.
CPC ........... *B01J 29/69* (2013.01); *B01J 29/7815* (2013.01); *C07C 29/50* (2013.01); *C07C 2529/69* (2013.01); *C07C 2529/78* (2013.01)

(58) Field of Classification Search
CPC ... B01J 35/30; B01J 37/12; B01J 37/14; B01J 2229/186; B01J 29/68; B01J 29/69; B01J 29/763; B01J 29/783; B01J 29/7215; B01J 29/7415; B01J 29/7815; Y02P 20/52; C07C 29/50; C07C 29/48; C07C 2529/69; C07C 2529/79; C07C 31/04
USPC ............. 502/60, 74; 562/542, 543, 544, 549
See application file for complete search history.

(56) References Cited

U.S. PATENT DOCUMENTS

| | | |
|---|---|---|
| 2015/0353840 A1 | 12/2015 | Hensley |
| 2016/0144338 A1 | 5/2016 | Elangovan |
| 2017/0107114 A1* | 4/2017 | Gounder ................. C01B 39/48 |
| 2017/0267616 A1 | 9/2017 | Roman-Leshkov |
| 2018/0319728 A1 | 11/2018 | Shan |

FOREIGN PATENT DOCUMENTS

| | | |
|---|---|---|
| CN | 101875016 A | 11/2010 |
| WO | 2011046621 A1 | 4/2011 |
| WO | 2016177542 A1 | 11/2016 |

OTHER PUBLICATIONS

International Search Report and Written Opinion for corresponding PCT application No. PCT/CZ2020/050018, dated Aug. 5, 2020.
International Preliminary Report on Patentability for corresponding PCT application No. PCT/CZ2020/050018, completed Jul. 19, 2021.
Pappas, Dimitrios, et al., "Understanding and Optimizing the Performance of Cu-FER for The Direct CH4 to CH3OH Conversion", 2019 Wiley-VCH Verlag Gmbh & Co. KGaA, WeinheimChemCatChem, Nov. 2019, 621-627.

* cited by examiner

*Primary Examiner* — Elizabeth D Wood
(74) *Attorney, Agent, or Firm* — Notaro, Michalos & Zaccaria P.C.

(57) ABSTRACT

The present invention relates to the use of a catalyst for production of methanol from methane, wherein the catalyst comprises a zeolite having Al pairs in the skeleton of at least 10 percent, based on the total number of all aluminium atoms in the zeolite, and further comprising a transition metal cation coordinated at beta-cationic positions, selected from the group consisting of Fe, Co, Mn, and Ni, wherein the ratio of the transition metal to Al is in the range of from 0.01 to 0.5; and with the proviso that the zeolite is not ZSM-5 and mordenite. The present invention further relates to the method of production of methanol, the catalyst for production of methanol by direct oxidation of methane, and to a method of production thereof.

3 Claims, No Drawings

USE OF A CATALYST FOR PRODUCTION OF METHANOL FROM METHANE, A METHOD OF PRODUCTION OF METHANOL FROM METHANE, THE CATALYST AND A METHOD OF PRODUCTION THEREOF

FIELD OF ART

The present invention relates to a zeolite-based catalyst for the production of methanol from methane, a method for its preparation, a method for producing methanol from methane and its use in the production of methanol without the need for subsequent extraction of methanol from zeolite with water or other reagents.

BACKGROUND ART

Direct conversion of methane to methanol is a potential way to easily exploit this abundant source of energy. The literature describes Cu-zeolites which have the potential to break a C—H bond in methane and convert it to methanol by hydrolysis. However, this conversion is still far from commercial use, since the materials used are poorly effective and a very high activation temperature (above 400° C.) is required for conversion. In addition, it is then necessary to extract the methanol from the zeolite by steam. Examples of such zeolites are Cu-MOR, Cu-ZSM-5 or Cu-SSZ-13.

WO 2016/177542 describes a method for preparing methanol from methane at a temperature of up to 280° C. using a zeolite-based catalyst, in particular Cu-MOR, Cu-ZSM-5 or zeolite Y or zeolite omega. The patent application proposes a process for the transformation of methane to methanol at temperatures below 280° C. and using molecular oxygen as an oxidant, characterized in that the primary product of methane oxidation is tightly bound to the catalyst and the methanol desorption occurs in a separate step in a stream of gas containing water, or of other reactive gas, namely CO. Cu-MOR is used as a catalyst, but zeolite Y or zeolite omega are also mentioned. The advantage of the method is that the entire process can be conducted isothermally at a temperature of up to 280° C. The reported yield of one operating cycle is very low, but can be increased by using a higher operating pressure, so that at 37 bar, about 56.2 μmol of methanol per gram of catalyst is achieved, but the use of higher pressures is not excluded. The main disadvantage of this process is that satisfactory yields cannot be achieved without the use of higher pressures, while of course the limit value for methane conversion is always limited by the potential concentration of the active centre, which is directly linked to the actual concentration of active metal and indirectly also to the limits given by the Si/Al value of the zeolite used.

WO 2011/046621 deals with the conversion of methane to methanol using Cu-zeolite. It describes low-temperature oxidation of methane on specific Cu-zeolite structure structurally characterized in detail as mono-(μ-oxo) dicopper core. This structure then ensures the oxidation of methane directly to methanol. The catalyst used can be regenerated to its original active state after each oxidation cycle. The main disadvantage of this process is the sensitivity of the active structure to even traces of moisture, so that not only the activated catalyst but also the entire oxidation process must take place in a perfectly dry environment.

Due to the limited concentration of the precisely defined active ingredient in the proposed Cu-zeolite, also the yield in one reaction cycle is low. In view of the required extremely low water vapour content, it can be expected that achieving this state will place demands on the necessary regeneration time of the catalyst, especially if some water molecules are produced due to less than 100 percent selectivity in methane oxidation.

US 2017/267616 A1 proposes a continuous catalytic process for the oxidation of methane using molecular oxygen and stably transforming methane into methanol at relatively low temperatures in a reaction mixture consisting of a mixture of methane, water vapour and oxygen. It proposes metallo-zeolites as catalysts, specifically Cu-ZSM-5 and Cu-MOR, although it also allows the use of other zeolites, namely FER and BEA, and does not exclude the use of other cations. Despite this broad definition of potentially active structures, the patent application in the structural specification of the process of very slow formation of unique active centres is based on migration of Cu ions, their reduction to Cu(I) and formation of Cu-dimers. As optimal for the gradual formation of an active structure, which is thus only incompletely specified, the patent application states a fundamental preference for ZSM-5 as optimal for the formation of this type of active centres.

It mentions molecular oxygen as the preferred oxidizing agent, but does not exclude other oxidizing agents, namely ozone, NO, $N_2O$ and/or $H_2O_2$, or combinations thereof.

Among the possible oxidized substrates, in addition to methane, it lists other linear and non-linear hydrocarbons of any structure (C1-C12 for linear, C3-C12 for non-linear), but does not specify them in the examples.

In addition to water as a protic solvent without which methanol is not extracted from the catalyst surface and thereby provides for the production of methanol, the document discloses the possible use of other protic solvents which can provide this reaction step, namely ethanol, formic acid or inorganic acids, such as HCl and $HNO_3$.

The main disadvantage of this process is in particular the very low conversion of methane, generally not reaching 0.02 percent and attempting to increase it only leads to a significant reduction in selectivity for the methanol formation, which is unsatisfactory even at low conversions and reaches values around 70 percent. As a result, the expected production of methanol per g of catalyst is small and does not reach technologically satisfactory values.

Pappas et al. (*ChemCatChem* 2019, 11, 621-627) describes Cu-FER zeolites and their use for the conversion of $CH_4$ to methanol. The zeolite was prepared by ion exchange and its catalytic activity strongly depends on the Cu/Al ratio. While at low Cu levels the catalyst is almost inactive, with increasing Cu/Al ratio its activity increases. The publication reports the Cu/Al ratio ranging from 0.11 to 0.20. The optimum activation temperature of the zeolite is given here as 500° C. It mentions the highest yield for Cu/Al 0.20, when the methanol yield is 88 μmol/g. Other types of zeolites used are Cu-MOR and Cu-ZSM. A persistent disadvantage of this arrangement is the low yield and high catalyst activation temperature.

CN 101875016 A discloses a catalyst for the preparation of methane by low temperature oxidation. The catalyst consists of a molecular sieve as a carrier containing an active ingredient, which contains copper oxides and a noble metal. Mentioned is Cu-ZSM-5, doped with platinum. Methanol is produced in an autoclave at a pressure of 1.5 MPa and 150° C. for 3 hours.

MAHYUDDIN, Muhammad Haris; SHIOTA, Yoshihito; YOSHIZAWA, Kazunari. Methane selective oxidation to methanol by metal-exchanged zeolites: a review of active sites and their reactivity. *Catalysis Science & Technology*, 2019, 9.8: 1744-1768; ISSN: 2044-4753; Chapters 3-6; describes zeolite catalysts Fe-ZSM-5, Fe-SSZ-13, Cu/Fe-ZSM-5, Cu-ZSM-5, Cu-MOR, Cu-SSZ-13, Cu-SSZ-16, Cu-SSZ-39, Cu-Omega, Co-ZSM-5, Ni-ZSM-5 to convert methane to methanol. Said catalysts are first activated with an oxidant at 250-500° C., then the conversion of methane to methanol takes place at 25-200° C. and the resulting methanol is then extracted with a suitable solvent or steam.

ZHAO, Guangyu; KENNEDY, Eric; STOCKENHUBER, Michael. Direct oxidation of methane to value-added products using $N_2O$ over Fe-ZSM-5, Fe-Beta and Fe-FER catalysts. In: *Proc., 8th Tokyo Conf. Adv. Catal. Sci. Technol. (TOCAT8)*. 2018, describes direct oxidation of methane using $N_2O$ and Fe-ZSM-5, Fe-Beta and Fe-FER catalysts at 350° C.

KRISNANDI, Yuni Krisyuningsih, et al. Partial oxidation of methane to methanol over heterogeneous catalyst Co/ZSM-5. *Procedia Chemistry*, 2015, 14: 508-515; ISSN: 1876-6196; describes the partial conversion of methane to methanol using Co-ZSM-5 as a catalyst. The catalyst was activated at 773 K (500° C.), the reaction was carried out with water vapour at 423 K (150° C.). The product was extracted with ethanol.

The various methods for preparing methanol from methane are summarized in the review Kulkarni, A. R. et al: Cation-exchanged zeolites for the selective oxidation of methane to methanol. *Catalysis Science & Technology* 2018, 8 (1), 114-123. A continuous or periodic process can be used to produce methanol. In the continuous process, the conversion in the methane/methanol system upon reaction with the oxidation centre is limited to values around ~0.01 percent, which substantially limits the possible application of the continuous process.

In the periodic process, on the other hand, the yield of one oxidation cycle is directly limited only by the concentration of the activated centre and the resulting hourly conversion of methane then by the length of the complete working cycle. Due to the fact that the current values of methanol yield per cycle are usually up to 160 µmol of methanol per g of catalyst (Grundner, S., M. A. C. Markovits, et al. (2015). "Single-site trinuclear copper oxygen clusters in mordenite for selective conversion of methane to methanol." Nature Communications 6.; Wulfers, M. J., S. Teketel, et al. (2015). "Conversion of methane to methanol on copper-containing small-pore zeolites and zeotypes." Chemical Communications 51(21): 4447-4450), and due to the fact that the usual length of the whole cycle is an hour or more, the average hourly methanol production does not reach satisfactory values.

DISCLOSURE OF INVENTION

The aim of the present invention is to provide a method of producing methanol from methane which increases the hitherto hourly yields of methanol mentioned in the prior art (generally expressed as methanol per gram of catalyst per hour) at low catalyst activation temperature and without the need to extract methanol with water or other solvent.

This object is achieved by providing a catalyst according to the present invention which allows the production of methanol from methane by direct oxidation, i.e. without the need for subsequent extraction of methanol from the catalyst with steam or other reagents, which further extends the time required for the entire cycle, or does not allow the process to be conducted under isothermal conditions. Thus, significantly higher hourly yields of methanol (based on grams of catalyst) are achieved than in the prior art, thanks to the optimal choice of active structure, which ensures a high concentration of specific active centre and realization of oxidation and production cycles at the same temperature not exceeding 300° C. This is achieved by a zeolite-based catalyst with a high concentration of a local paired cationic structure, where the Fe, Co, Mn or Ni cations can serve as the active cation.

Thus, the catalyst of the present invention contains a high density of active centres.

The zeolite is based on $SiO_4$ and $AlO_4$ tetrahedra, which are interconnected by sharing peak oxygens. The aluminium atoms in the zeolite exist as paired (so-called "Al pairs" located in one ring of the zeolite) and unpaired (so-called "unpaired Al atoms" and "single Al atoms" located in two different rings of the zeolite). The high concentration of the local paired cationic structure of the zeolite means that the zeolite contains a high amount of paired aluminium atoms, in particular at least 10 percent of the number of all Al atoms in the skeleton are paired, i.e. located always two in one ring of the zeolite. This arrangement allows a smaller distance of two adjacent cations of transition metal (the high concentration of active centre as the main product of interaction between the metal cation and the zeolite) contained in the zeolite structure and hence the specific catalytic properties of the zeolite of the present invention. The actual total Al content in the zeolite, expressed as a percentage by weight, is about 3.5 to 4 percent, corresponding to a Si to Al ratio in the range of 2 to 9, preferably in the range of 4 to 9.

In addition, the method for producing methanol from methane according to the present invention has a shorter overall duration of the entire reaction cycle, because the whole process is isothermal, which leads to an increase in the hourly yield of methanol. The catalyst contains a high concentration of active centre as the main product of the interaction between the metal cation and the zeolite, which ensures easy activation of molecular oxygen already at low temperatures. After oxidation, an active material with a high concentration of oxidized active centre is formed for easy activation of methane and its desorption in the form of methanol.

One object of the present invention is the use of a catalyst for the production of methanol from methane, the catalyst comprising a zeolite having Al pairs in the skeleton of at least 10 percent based on the total number of all aluminium atoms in the zeolite, and comprising a transition metal cation coordinated at beta-cationic positions, selected from the group consisting of V, Cr, Mn, Fe, Co, Ni, Cu, Ag, preferably from the group consisting of Fe, Co, Mn and Ni, wherein the ratio of the transition metal to Al is in the range of from 0.01 to 0.5, preferably in the range of from 0.25 to 0.4. The paired structure corresponds to two divalent cations of transition metal coordinated at two adjacent cationic positions allowing the two cations to function as one binuclear centre, corresponding to a distance of these two transition metal cations ranging from 4.5 to 12 Å, preferably from 6 to 9 Å, more preferably 7.4 Å. The distance between the two transition metal cations was determined based on a DFT (density-functional theory) model based on X-ray diffraction of zeolite. Each cation is compensated by two aluminium atoms in the ring forming a cationic position. Any zeolite can be used which allows the formation of binuclear centres composed of two cations coordinated at two such cationic positions which allow the functioning of binuclear centres, for example zeolites of FER, *BEA, FAU, SSZ-13, MWW, LTA, GME, LEV and OFF types, optionally also of CHA topology with a Si/Al ratio in the range of 2 to 9, more preferably in the range of 2 to 5. The Si/Al ratio for FER,

*BEA, FAU, SSZ-13, MWW, LTA, GME, LEV and OFF is preferably in the range of 2 to 9, more preferably in the range of 4 to 9. Preferably, the zeolite is ferrierite (FER), zeolite beta (BEA) or SSZ-13. Examples of zeolites for which this arrangement is structurally NOT possible are zeolites ZSM-5 (MFI) and mordenite (MOR). The number of Al pairs for the zeolites used was determined by a method based on a quantitative analysis of the extent of formation of Co(II) complexes characterized by a combination of chemical analysis, FTIR and UV Vis spectroscopy. Details of the method are described in the publication J. Dědeček, Z. Sobalík, B. Wichterlová, *Siting and Distribution of Framework Aluminium Atoms in Silicon-Rich Zeolites and Impact on Catalysis*, Catalysis Reviews: Science and Engineering 54 (2012) 135-223.

In a preferred embodiment, the catalyst zeolite contains at least 20 percent of Al pairs in the skeleton, based on the total number of all aluminium atoms in the zeolite, preferably at least 30 percent of Al pairs in the skeleton, based on the total number of all aluminium atoms in the zeolite, more preferably at least 35 percent of Al pairs in the skeleton, based on the total number of all aluminium atoms in the zeolite, even more preferably at least 40 percent of Al pairs in the skeleton, based on the total number of all aluminium atoms in the zeolite, even more preferably at least 50 percent of Al pairs in the skeleton, based on the total number of all aluminium atoms in the zeolite, and most preferably at least 60 percent of Al pairs in the skeleton, based on the total number of all aluminium atoms in the zeolite.

In one preferred embodiment, the zeolite according to the Nickel-Strunz classification is a zeolite of the FER, BEA or SSZ-13 types, preferably a zeolite of the FER type.

The above use of catalysts of the present invention in comparison with the prior art Cu-FER catalyst (Pappas et al. (ChemCatChem 2019, 11, 621-627), which does not contain Al pairs in the skeleton of at least 10 percent, based on the total number of all aluminium atoms in the zeolite, shows a 2 to 2.25 times higher yield (based on grams of catalyst). In addition, due to the more favourable temperature regime during the reaction cycle of the present invention, it is possible to perform up to four cycles per hour instead of one, which significantly increases the hourly yield of methanol.

Another object of the present invention is a method for the production of methanol which comprises following steps:
(i) the catalyst for the production of methanol from methane is oxidized with oxygen at a temperature of at most 300° C., preferably at most 250° C., more preferably in the range of from 20 to 200° C.;
wherein the catalyst comprises a zeolite containing Al pairs in the skeleton of at least 10 percent, based on the total number of aluminium atoms in the zeolite, and containing a transition metal cation coordinated at beta-cationic positions, selected from the group of transition metals selected from the group consisting of V, Cr, Mn, Fe, Co, Ni, Cu and Ag, wherein the ratio of transition metal to Al is in the range of 0.01 to 0.5, preferably in the range of 0.25 to 0.4. The paired structure corresponds to two divalent cations of transition metal coordinated at two adjacent cationic positions allowing the two cations to function as one binuclear centre, corresponding to a distance of these two transition metal cations ranging from 4.5 to 12 Å, preferably from 6 Å to 9 Å. Each transition metal cation is compensated by two aluminium atoms in the ring forming a cationic position. Any zeolite can be used which allows the formation of binuclear centres composed of two cations coordinated at two such cationic positions which allow the functioning of binuclear centres, for example zeolites of topological types: FER, *BEA, FAU, SSZ-13, MWW, LTA, GME, LEV and OFF, or also of CHA topology with a Si/Al ratio in the range of 2 to 9, but most preferably with a Si/Al ratio value in the range of 2 to 5. The Si/Al ratio for FER, *BEA, FAU, SSZ-13, MWW, LTA, GME, LEV and OFF is preferably in the range of 2 to 9, more preferably in the range of 4 to 9;
(ii) the oxidized catalyst is contacted with methane with which it interacts to form methanol at the same temperature as in step (i), i.e. at most 300° C., preferably at most 250° C., more preferably in the range of 20 to 200° C.

Preferably, the temperature in both steps is 200° C.
Preferably, the catalyst is activated before step (i) in a stream of oxygen (preferably 25 ml/min for at least 1 hour), followed by helium (preferably 25 ml/min for a further 2 hours) at a temperature of at least 450° C.

Another object of the present invention is a catalyst for the production of methanol from methane which comprises a zeolite having Al pairs in the skeleton of at least 10 percent, based on the total number of aluminium atoms in the zeolite, and a transition metal cation coordinated at beta-cationic positions, selected from the group consisting of V, Cr, Mn, Fe, Co, Ni, Cu, Ag, wherein the ratio of transition metal to Al is in the range of 0.01 to 0.5, preferably in the range of 0.25 to 0.4.

The paired structure corresponds to two divalent transition metal cations coordinated at two adjacent cationic positions allowing the two cations to function as one binuclear centre, which corresponds to a distance of these two transition metal cations ranging from 4.5 to 12 Å, preferably from 6 Å to 9 Å. Each transition metal cation is compensated by two aluminium atoms in the ring forming a cationic position. Any zeolite can be used which allows the formation of binuclear centres composed of two cations coordinated at two such cationic positions which allow the functioning of binuclear centres, for example zeolites of following topological types: FER, *BEA, FAU, MWW, LTA, GME, LEV and OFF, or also of CHA topology with a Si/Al ratio in the range of 2 to 9, but most preferably with a Si/Al ratio value in the range of 2 to 5. The Si/Al ratio for FER, *BEA, FAU, SSZ-13, MWW, LTA, GME, LEV and OFF is preferably in the range of 2 to 9, more preferably in the range of 4 to 9.

An example of a zeolite for which this arrangement is NOT possible is ZSM-5 zeolite (MFI) and mordenite (MOR).

In one preferred embodiment, the zeolite according to the Nickel-Strunz classification is a zeolite of the FER, BEA or SSZ-13 types, preferably a zeolite of the FER type.

Another object of the present invention is a method for the preparation of the catalyst according to the present invention, which comprises following steps:
a) a dried zeolite, selected from the group consisting of topological types FER, *BEA, FAU, SSZ-13, MWW, LTA, GME, LEV and OFF, or also of the CHA topology with a Si/Al ratio ranging from 2 to 9, is impregnated with a cation solution of a transition metal selected from the group consisting of V, Cr, Mn, Fe, Co, Ni, Cu and Ag, preferably selected from the group consisting of Fe, Co, Mn and Ni;
b) the impregnation solution is removed and the resulting catalyst is dried.

Preferably, an aqueous or acetylacetone solution of $FeCl_3$, $FeSO_4$, $Co(NO_3)_2$, $CoAc_2$, $Ni(NO_3)_2$ or $Mn(NO_3)_2$ is used as the transition metal cation solution. The impregnation takes place at room temperature (25° C.) or elevated temperature, preferably at 60° C.

Preferably, step (a) is repeated with fresh impregnation solution, more preferably step (a) is repeated at least twice for 24 hours, more preferably three times for 24 hours.

The drying of the catalyst in step (b) can take place on air or under an inert atmosphere (e.g. $N_2$) at atmospheric pressure. The average drying time is at least 4 hours. Drying takes place at room temperature or can take place at elevated temperatures, e.g. at 350° C.

Preferably, the zeolite is ferrierite (FER), BEA or SSZ-13 and the transition metal is Fe, Co, Ni, Mn, Cu. Most preferably, the zeolite is Fe-FER, Co-FER, Ni-FER, Mn-FER, Co-*BEA, Fe-SSZ-13.

Optionally, step (b) may be followed by step (c), in which the resulting catalyst is calcined under air and at a temperature of at least 400° C., preferably at least 420° C., more preferably at 450° C.

EXAMPLES

Materials

Ferrierite, BEA zeolite and SSZ-13 zeolite were used as starting zeolites for the synthesis of catalysts of the present invention.

If ferrierite was used, it was obtained as follows

The commercially available ferrierite was obtained from TOSOH or prepared as follows (designated FER (HI)):

3.0 g of sodium aluminate, 80 g of water and 0.4 g of NaOH were mixed, and after 15 minutes, 17 g of pyrrolidine was added to the resulting solution, and the mixture was further stirred for another 15 minutes. Then 90 g of colloidal silica, 30 wt. % suspension in water (LUDOX-30) was added and the mixture was stirred until homogenized. The synthesis gel thus prepared was placed in a stainless steel autoclave with a Teflon liner and heated at 145° C. for 15 days. The obtained zeolite was thoroughly washed with water and dried. To remove residual organic templates, the resulting ferrierite was calcined at 450° C. for 5 hours in a stream of air.

Ferrierite (TOSOH) had the following parameters: Si/Al 8.5; 66 percent of the number of all Al present was in the form of Al pairs; 45 percent of the number of all Al present in the form of a pair of adjacent Al pairs. A pair of adjacent Al pairs is defined as a pair of Al pairs that form two adjacent cationic sites in which, after being occupied by a pair of cations, this pair of cations is spaced 4.5 to 12 Å apart.

The ferrierite prepared by the above procedure (designated FER (HI)) had the following parameters:
Si/Al 9; 56 percent of the number of all Al present in the form of Al pairs; 35 percent of the number of all Al present in the form of a pair of adjacent Al pairs.

If BEA zeolite was used, it was synthesized as follows 10 g of $NaAlO_2$ was dissolved in 1000 ml of deionized water, followed by addition of 42 g of NaOH and stirring for 40 minutes, addition of 96 g of micronized silica (Cabosil), stirring for 10 minutes and addition of 5 g of beta zeolite nuclei. The mixture was then homogenized for 5 minutes. The synthesis was performed in a 2500 ml unstirred autoclave at 120° C. for 125 hours under autogenous pressure. The zeolite product was washed with deionized water and dried at 80° C. for 6 hours. The dried synthesized zeolite was calcined for 8 hours in a stream of air at 540° C.

BEA zeolite had the following parameters: Si/Al 4.5; 30 percent of the number of all Al present in the form of Al pairs; 30 percent of the number of all Al present in the form of a pair of adjacent Al pairs.

If SSZ-13 zeolite was used, it was synthesized as follows
SSZ-13 Si/Al 4.5

5 g of sodium silicate (26.5 percent by weight of $SiO_2$) (SIGMA-Aldrich) were added to 60 g of deionized water and stirred for 15 minutes, then 1 g of zeolite Y (in the form of Na, Si/Al=2.5) was added and further stirred for 30 minutes. 13.15 g of 20 percent by weight of TMAdOH (tetramethylammonium hydroxide, Chinese supplier) were added and stirred for another 30 minutes and then the synthetic mixture was placed in an autoclave for 6 days at 140° C. with rotation.

The synthesized SSZ-13 had the following parameters: Si/Al 4.5; 50 percent of the number of all Al present in the form of Al pairs; 40 percent of the number of all Al present in the form of a pair of adjacent Al pairs.

SSZ-13 Si/Al 5.5

5 g of sodium silicate (26.5 percent by weight of $SiO_2$) (SIGMA-Aldrich) was added to 60 g of deionized water and stirred for 15 minutes, then 2.1 g of zeolite $Al_2(SO_4)_3$ was added and further stirred for 30 minutes. 13.15 g of 20 percent by weight of TMAdOH (Chinese supplier) were added and stirred for another 30 minutes, and then the synthetic mixture was placed in an autoclave for 6 days at 140° C. with rotation.

The synthesized SSZ-13 had the following parameters: Si/Al 5.5: 40 percent of the number of all Al present in the form of Al pairs; 35 percent of the number of all Al present in the form of a pair of adjacent Al pairs.

Characteristics of Catalysts

The number of Al pairs for the zeolites used was determined by a method based on a quantitative analysis of the extent of formation of Co(II) complexes characterized by a combination of chemical analysis, FTIR and UV Vis spectroscopy. Details of the method are described in the publication J. Děděček, Z. Sobalik, B. Wichterlová, *Siting and Distribution of Framework Aluminium Atoms in Silicon-Rich Zeolites and Impact on Catalysis*, Catalysis Reviews: Science and Engineering 54 (2012) 135-223.

The frequency of optimal local arrangements, comprising two pairs of adjacent pairs always with a total of four Al atoms and necessary for the formation of binuclear metal ion centres, was derived for each zeolite from the Si/Al value, the frequency of Al pairs and the known zeolite topology.

Example 1: Catalytic Test (Same for all Samples)

The products of the catalytic reaction were monitored by mass spectrometry. Uniform distribution of the catalyst particles in the range of 600 to 300 μm was achieved by pressing, crushing and sieving the powders. In a quartz reactor, 0.25 to 0.50 g of catalyst sample was used for the test. A tube furnace with temperature controlled by a thermocouple was used for the reaction. Prior to the first reaction cycle, the catalyst sample was heated in a stream of oxygen (25 ml/min) at 450° C. for 1 h, and then in a stream of helium (25 ml/min) for another 2 hours at the same temperature. Then, the temperature was reduced in a stream of inert gas (ramp 10° C./min) to 200° C.

Subsequently, catalytic cycles of methane oxidation were performed. The sample was exposed to a stream of oxygen (25 ml/min) for 10 minutes, purged with argon (25 ml/min) for 1 min. The interaction with $CH_4$ (25 ml/min) lasted for 5 minutes and then the reactor was purged with a stream of inert gas for 1 minute. Signals were detected for m/z=31 for methanol, m/z=29 for other possible oxidation products, such as formaldehyde, formic acid, dimethyl ether and m/z=44 for $CO_2$. The signal m/z=31 was integrated and compared with the calibration data for methanol to quantify the methanol yield. The cycles were repeated five times without the observed decrease in methanol yield.

Example 2: Fe-FER (TOSOH) Catalyst (Fe/Al 0.03)

Fe-FER zeolite, Si/Al 8.5, Fe/Al 0.03 was prepared by impregnation with a solution of $FeCl_3$ in acetylacetone (AcAc). For this purpose, a granulated sample of $NH_4$-FER (TOSOH) (particle size from 600 to 300 μm) was dehydrated for 4 hours at 120° C. in a stream of air (25 ml/min). To 1 g of dehydrated zeolite an impregnation solution composed of 0.10 g of $FeCl_3$ and 1.70 g of AcAc was added and left overnight at room temperature. The next day, the excess impregnation solution was removed by filtration. The sample thus prepared was heated under dynamic vacuum as follows: 1 h at 100° C. and then 3 h at 350° C. (heating rate 4° C./min). After cooling to room temperature, the sample was filtered off and washed with distilled water, then dried at room temperature.

The material thus prepared was calcined in air at 450° C. for 24 hours.

In the reaction test according to Example 1, 170 μmol of methanol per gram of catalyst per hour were obtained, and at the same time 20 μmol of a mixture of formaldehyde and dimethyl ether (i.e. oxygenates) per gram of catalyst per hour.

Example 3: Fe-FER (TOSOH) Catalyst (Fe/Al 0.25)

Fe-ferrierite, Fe/Al 0.25 was prepared by impregnation with a solution of $FeCl_3$ in acetylacetone (AcAc). For this purpose, a granulated sample of $NH_4$-FER (TOSOH) (particle size from 600 to 300 μm) was dehydrated for 4 hours at 120° C. in a stream of air (25 ml/min). To 1 g of dehydrated zeolite an impregnation solution composed of 0.82 g of $FeCl_3$ and 14.20 g of AcAc was added and left overnight at room temperature. The next day, the excess impregnation solution was removed by filtration. The sample thus prepared was heated under dynamic vacuum as follows: 1 h at 100° C. and then 3 h at 350° C. (heating rate 4° C./min). After cooling to room temperature, the sample was filtered off and washed with distilled water, then dried at room temperature.

The material thus prepared was calcined in air at 450° C. for 24 hours.

In the reaction test according to Example 1, 1600 μmol of methanol per gram of catalyst per hour were obtained, and at the same time 400 μmol of a mixture of formaldehyde and dimethyl ether per gram of catalyst per hour.

Example 4: Fe-FER (TOSOH) Catalyst (Fe/Al 0.30)

Fe-ferrierite, Fe/Al 0.30 was prepared by ion exchange with aqueous $FeSO_4$ solution. 1 g of the sample was changed twice for 12 h with 100 ml of 0.05 M $FeSO_4$ solution. Before preparing the solution, oxygen was removed from the distilled water used by bubbling with a stream of nitrogen for 1 hour. The ion exchange took place in a closed vessel and under a nitrogen atmosphere. The sample was then centrifuged under nitrogen and dried in a stream of nitrogen at room temperature. In the reaction test according to Example 1, 1800 μmol of methanol per gram of catalyst per hour and 500 μmol of a mixture of formaldehyde and dimethyl ether per gram of catalyst per hour were obtained.

Example 5: Fe-FER (TOSOH) Catalyst (Fe/Al 0.45)

Fe-FER zeolite, Si/Al 8.5, Fe/Al 0.45 was prepared by impregnation with a solution of $FeCl_3$ in acetylacetone (AcAc). For this purpose, a granulated sample of $NH_4$-FER (TOSOH) (particle size from 600 to 300 μm) was dehydrated for 4 hours at 120° C. in a stream of air (25 ml/min). To 1 g of dehydrated zeolite an impregnation solution composed of 1.48 g of $FeCl_3$ and 25.56 g of AcAc was added and left overnight at room temperature. The next day, the excess impregnation solution was removed by filtration. The sample thus prepared was heated under dynamic vacuum as follows: 1 h at 100° C. and then 3 h at 350° C. (heating rate 4° C./min). After cooling to room temperature, the sample was filtered off and washed with distilled water, then dried at room temperature and calcined in air at 450° C. for 24 hours.

In the reaction test according to Example 1, 680 μmol of methanol per gram of catalyst per hour and 90 μmol of a mixture of formaldehyde and dimethyl ether per gram of catalyst per hour were obtained.

Example 6: Co-FER (TOSOH) Catalyst (Co/Al 0.15)

Co-FER zeolite, Si/Al 8.5, Co/Al 0.15 was prepared by ion exchange of a powder sample of $NH_4$-FER (TOSOH) with a 0.05 M aqueous solution of $Co(NO_3)_2.6H_2O$ at 60° C. (1×12 h, 50 ml solution/1 g zeolite). After ion exchange, the zeolite was thoroughly washed and air dried at room temperature.

In the reaction test according to Example 1, 150 μmol of methanol per gram of catalyst per hour and ~20 μmol of a mixture of formaldehyde and dimethyl ether per gram of catalyst per hour were obtained.

Example 7: Co-FER (TOSOH) Catalyst Co/Al 0.30

Co-FER zeolite, Si/Al 8.5, Co/Al 0.15 was prepared by ion exchange with 0.05 M aqueous cobalt acetate solution at 60° C. (3×24 h, 100 ml solution/1 g zeolite). The sample was then washed thoroughly and air dried at room temperature.

In the reaction test according to Example 1, 900 μmol of methanol per gram of catalyst per hour and 60 μmol of a mixture of formaldehyde and dimethyl ether per gram of catalyst per hour were obtained.

Example 8: Co-FER (TOSOH) Catalyst (Co/Al 0.35)

Co-FER zeolite, Si/Al 8.5, Co/Al 0.35 was prepared by ion exchange with $CoAc_2$. 1.0 g of $NH_4$-FER (TOSOH) was added to 100 ml of 0.05 M aqueous $CoAc_2$ solution and stirred at 70° C. for 12 hours. This procedure was repeated three times. Subsequently, the obtained material was filtered off and washed thoroughly with distilled water and then dried at room temperature. The dried sample was heated to 450° C. in a stream of air for 24 hours.

In the reaction test according to Example 1, 1900 μmol of methanol per gram of catalyst per hour were obtained, and at the same time 200 µmol of a mixture of formaldehyde and dimethyl ether per gram of catalyst per hour.

Example 9: Co-FER (TOSOH) Catalyst (Co/Al 0.44)

Co-FER zeolite, Si/Al 8.5, Co/Al 0.44 was prepared by ion exchange with 0.05 M aqueous solution of $Co(NO_3)_2$ at 60° C. (3×12 h, 50 ml solution/1 g zeolite). After ion exchange, the zeolite was thoroughly washed and air dried at room temperature.

In the reaction test according to Example 1, 550 µmol of methanol per gram of catalyst and 50 µmol of a mixture of formaldehyde and dimethyl ether per gram of catalyst per hour were obtained.

Example 10: Ni-FER (TOSOH) Catalyst (Ni/Al 0.18)

Ni-FER zeolite, Si/Al 8.5, Ni/Al 0.18 was prepared by ion exchange with 0.05 M aqueous solution of $Ni(NO_3)_2.6H_2O$ at 30° C. (1×12 h, 50 ml solution/1 g zeolite). After ion exchange, the zeolite was thoroughly washed and air dried at room temperature.

In the reaction test according to Example 1, 100 µmol of methanol per gram of catalyst and ~30 µmol of a mixture of formaldehyde and dimethyl ether per gram of catalyst per hour were obtained.

Example 11: Ni-FER (TOSOH) Catalyst (Ni/Al 0.32)

Ni-FER zeolite, Si/Al 8.5, Ni/Al 0.32 was prepared by impregnation with an aqueous solution of $Ni(NO_3)_2$. A granulated sample of $NH_4$-FER (TOSOH) (particle size from 600 to 300 µm) was dehydrated for 4 hours at 120° C. in a stream of air (25 ml/min). 1 ml of a solution of $Ni(NO_3)_2.6H_2O$ with a concentration of 2.0 wt. % was added dropwise to the zeolite. The sample was then air dried for 24 hours at room temperature and then calcined in air at 450° C. for 4 hours. In the reaction test according to Example 1, 1700 µmol of methanol per gram of catalyst per hour were obtained, and at the same time 550 µmol of a mixture of formaldehyde and dimethyl ether per gram of catalyst per hour.

Example 12: Ni-FER (TOSOH) Catalyst (Ni/Al 0.45)

Ni-FER zeolite, Si/Al 8.5, Ni/Al 0.45 was prepared by impregnating granulated $NH_4$-FER (TOSOH) (particle size from 600 to 300 µm) being dehydrated for 4 hours at 120° C. in a stream of air (25 ml/min). The solution of 0.28 g $Ni(NO_3)_2.6H_2O$ in 1 ml of water was added dropwise to the zeolite. The sample was then air dried for 24 hours at room temperature and then calcined in air at 450° C. for 4 hours.

In the reaction test according to Example 1, 570 µmol of methanol per gram of catalyst and 130 µmol of a mixture of formaldehyde and dimethyl ether per gram of catalyst per hour per hour were obtained,

Example 13: Mn-FER (TOSOH) Catalyst (Mn/Al 0.16)

Mn-FER zeolite, Si/Al 8.5, Mn/Al 0.16 was prepared by ion exchange with 0.05 M aqueous solution of $Mn(NO_3)_2$ at 60° C. (1×12 h, 50 ml solution/1 g zeolite). After ion exchange, the zeolite was thoroughly washed and air dried at room temperature.

In the reaction test according to Example 1, 80 µmol of methanol per gram of catalyst and 15 µmol of a mixture of formaldehyde and dimethyl ether per gram of catalyst per hour were obtained.

Example 14: Mn-FER (TOSOH) Catalyst (Mn/Al 0.28)

Mn-FER zeolite, Si/Al 8.5, Mn/Al 0.28, was prepared by ion exchange with 0.05 M aqueous solution of $Mn(NO_3)_2$. 1.0 g of $NH_4$-FER (TOSOH) was added to 100 ml of a 0.05 M aqueous solution of $Mn(NO_3)_2$ and stirred at 70° C. for 12 hours. This procedure was repeated three times. After ion exchange, the obtained material was filtered off and washed thoroughly with distilled water and then dried at room temperature.

In the reaction test according to Example 1, 1500 µmol of methanol per gram of catalyst per hour and at the same time 350 µmol of a mixture of formaldehyde and dimethyl ether per gram of catalyst per hour were obtained.

Example 15: Mn-FER (TOSOH) Catalyst (Mn/Al 0.35)

Mn-FER zeolite, Si/Al 8.5, Mn/Al 0.35, was prepared by impregnation with an aqueous solution of $Mn(NO_3)_2$. A granulated sample of $NH_4$-FER (TOSOH) (particle size from 600 to 300 µm) was dehydrated for 4 hours at 120° C. in a stream of air (25 ml/min).

A solution containing 2.0 wt. % of $Mn(NO_3)_2.4H_2O$ in an amount of 1 ml per gram of zeolite was added dropwise to the dried zeolite. The sample was then air dried for 24 hours at room temperature and then calcined in air at 450° C. for 4 hours.

In the reaction test according to Example 1, 1800 µmol of methanol per gram of catalyst per hour and at the same time 600 µmol of a mixture of formaldehyde and dimethyl ether per gram of catalyst per hour were obtained.

Example 16: Co-*BEA Catalyst (Co/Al 0.30)

1.0 g of zeolite $NH_4$-beta with Si/Al 4.5 was added to 100 ml of a 0.05 M aqueous solution of $Co(NO_3)_2$ and the mixture was stirred at room temperature for 12 hours. The zeolite was then filtered off and washed thoroughly with distilled water and dried at room temperature.

In the reaction test according to Example 1, 450 µmol of methanol per gram of catalyst per hour and at the same time 40 µmol of a mixture of formaldehyde and dimethyl ether per gram of catalyst per hour were obtained.

Example 17: Co-*BEA Catalyst (Co/Al 0.50)

1.0 g of zeolite $NH_4$-beta with Si/Al 4.5 was added to 100 ml of a 0.05 M aqueous solution of $CoAc_2$ and the mixture was stirred at room temperature for 12 hours. This procedure was repeated three times. The zeolite was then filtered off and washed thoroughly with distilled water and dried at room temperature.

Subsequently, the material was heated to 450° C. in a stream of air for 24 hours.

In the reaction test according to Example 1, 550 µmol of methanol per gram of catalyst per hour and at the same time

Example 18: Fe-SSZ-13 Catalyst (Fe/Al 0.1)

Fe-SSZ-13 zeolite, Si/Al 4.5, Fe/Al 0.1 was prepared by impregnation with acetylacetone. A granulated sample of $NH_4$-SSZ-13 (particle size from 600 to 300 µm) was dehydrated for 4 hours at 120° C. in a stream of air (25 ml/min). To 1 g of dehydrated zeolite an impregnation solution composed of 0.10 g of $FeCl_3$ and 1.70 g of AcAc was added and left overnight at room temperature. The next day, the excess impregnation solution was removed by filtration. The sample thus prepared was heated under dynamic vacuum as follows: 1 h at 100° C. and then 3 h at 350° C. (heating rate 4° C./min). After cooling to room temperature, the sample was filtered off and washed with distilled water, then dried at room temperature and calcined in air at 450° C. for 24 hours.

In the reaction test according to Example 1, 250 µmol of methanol per gram of catalyst and at the same time ~30 µmol of a mixture of formaldehyde and dimethyl ether per gram of catalyst per hour were obtained.

Example 19: Fe-SSZ-13 Catalyst Fe/Al 0.15

SSZ-13 zeolite, Si/Al 5.5 Fe/Al 0.15 was prepared by impregnation with acetylacetone. A granulated sample of $NH_4$-SSZ-13 (particle size from 600 to 300 µm) was dehydrated for 4 hours at 120° C. in a stream of air (25 ml/min). To 1 g of dehydrated zeolite an impregnation solution composed of 0.10 g of $FeCl_3$ and 1.70 g of AcAc was added and left overnight at room temperature. The next day, the excess impregnation solution was removed by filtration. The sample thus prepared was heated under dynamic vacuum as follows: 1 h at 100° C. and then 3 h at 350° C. (heating rate 4° C./min). After cooling to room temperature, the sample was thoroughly filtered off and washed with distilled water, then dried at room temperature and calcined in air at 450° C. for 24 hours.

In the reaction test according to Example 1, 220 µmol of methanol per gram of catalyst and at the same time ~30 µmol of a mixture of formaldehyde and dimethyl ether per gram of catalyst per hour were obtained.

Example 20: Fe-FER (HI) Catalyst (Fe/Al 0.28)

Fe-ferrierite, Si/Al 9, Fe/Al 0.28 was prepared by ion exchange with aqueous $FeSO_4$ solution. 1 g of the sample was changed twice for 12 h with 100 ml of 0.05 M $FeSO_4$ solution. Before preparing the solution, oxygen was removed from the distilled water used by bubbling with a stream of nitrogen for 1 hour. The ion exchange took place in a closed vessel and under a nitrogen atmosphere. The sample was then centrifuged under nitrogen and dried in a stream of nitrogen at room temperature.

In the reaction test according to Example 1, 800 µmol of methanol per gram of catalyst per hour and 50 µmol of a mixture of formaldehyde and dimethyl ether per gram of catalyst per hour were obtained.

Example 21: Comparison of the Catalysts of the Present Invention with the Cu-FER Catalyst of the Publication Pappas et al., ChemCatChem 2019, 11, 621-627

The catalysts prepared according to Examples 8 and 11 of the present invention were compared with the Cu-FER catalyst according to the above publication. The test was performed according to Example 1. The Cu-FER catalyst of the prior art had a Cu to Al ratio of 0.2, a Si to Al ratio of 10 and an hourly yield of methanol per gram of this catalyst was very low. In comparison, the production of methanol per cycle for the catalysts according to the present invention was about 10 times higher and with regard to the possibility of repeating the production cycle in the case of the present invention up to 4 times per hour, with regard to the very long cycle in said publication (about 18 hours), the process according to the present invention gives incomparably higher average hourly methanol production.

The invention claimed is:

1. A catalyst for the production of methanol from methane,
    wherein the catalyst comprises a zeolite having at least 10 percent of Al atoms in the skeleton located in pairs, each pair represented by two Al atoms located in one ring of the zeolite, based on the total number of all aluminium atoms in the zeolite, the number of Al pairs determined by a method based on a quantitative analysis of the extent of formation of Co(II) complexes characterized by a combination of chemical analysis, FTIR and UV Vis spectroscopy, and
    further comprising a divalent transition metal cation M, wherein the distance of two adjacent divalent transition metal cations coordinated at two adjacent cationic positions forming one binuclear centre is in the range of from 6 to 9 Å, determined using DFT model based on X-ray diffraction of the zeolite, wherein M is selected from the group consisting of Mn, Fe, Co, and Ni,
    wherein the ratio of the transition metal M to Al is in the range of from 0.01 to 0.5,
    wherein the Si/Al ratio is in the range of from 2 to 9, and
    wherein the zeolite is selected from the group consisting of ferrierite, beta zeolite and SSZ-13, according to the Nickel-Strunz classification.

2. A method for production of methanol, characterized in that it comprises the following steps:
    (i) a catalyst for production of methanol from methane is oxidized with oxygen at a temperature of at most 300° C.,
    wherein the catalyst comprises a zeolite having at least 10 percent of Al atoms in the skeleton located in pairs, each pair represented by two Al atoms located in one ring of the zeolite, based on the total number of aluminium atoms in the zeolite, the number of Al pairs determined by a method based on a quantitative analysis of the extent of formation of Co(II) complexes characterized by a combination of chemical analysis, FTIR and UV Vis spectroscopy,
    and containing a transition metal cation M, wherein the distance of two adjacent divalent transition metal cations coordinated at two adjacent cationic positions forming one binuclear centre is in the range of from 6 to 9 Å, determined using DFT model based on X-ray diffraction of the zeolite, wherein M is selected from the group consisting of Mn, Fe, Co, and Ni,
    wherein the ratio of the transition metal M to Al is in the range of from 0.01 to 0.5,
    wherein the Si to Al ratio is in the range of from 2 to 9, and
    wherein the zeolite is selected from the group consisting of ferrierite, beta zeolite and SSZ-13, according to the Nickel-Strunz classification; and (ii) the oxidized catalyst is contacted with methane with which it interacts to form methanol at the same temperature as in step (i).

3. The method for production of methanol according to claim 2, wherein the catalyst is activated before step (i) in a stream of oxygen, followed by helium at a temperature of at least 450° C.

* * * * *